United States Patent
Hasegawa et al.

[11] Patent Number: 6,083,931
[45] Date of Patent: Jul. 4, 2000

[54] METHOD OF INHIBITING CANCER METASTASIS

[75] Inventors: Takaaki Hasegawa, Gifu; Kenichi Miyamoto, Kanazawa; Mitsuo Kawase, Nagoya; Yasuko Yoshida, Nagoya; Tadahiko Inukai, Nagoya, all of Japan

[73] Assignees: NGK Insulators, Ltd.; Biseiken Co., Ltd., Japan

[21] Appl. No.: 08/930,680

[22] PCT Filed: Feb. 8, 1996

[86] PCT No.: PCT/JP96/00268

§ 371 Date: Dec. 9, 1997

§ 102(e) Date: Dec. 9, 1997

[87] PCT Pub. No.: WO97/28807

PCT Pub. Date: Aug. 14, 1997

[51] Int. Cl.[7] .................................................. A61K 31/715
[52] U.S. Cl. .................. 514/54; 514/53; 514/23; 514/61; 536/18.7; 536/123.1
[58] Field of Search .................. 514/23, 53, 54, 514/61; 536/18.7, 123.1

[56] References Cited

FOREIGN PATENT DOCUMENTS

| 502 827 A1 | 9/1992 | European Pat. Off. |
| 521 692 A2 | 7/1993 | European Pat. Off. |
| 2 560 881 | 9/1985 | France. |
| 60-190791 | 9/1985 | Japan. |
| 61-83125 | 4/1986 | Japan. |
| 62-132895 | 6/1987 | Japan. |
| 62-223124 | 10/1987 | Japan. |
| 3-245784 | 9/1994 | Japan. |
| Wo 92/18610 | 10/1992 | WIPO. |
| WO 95/21618 | 8/1995 | WIPO. |

OTHER PUBLICATIONS

The Merck Index, Ninth Edition, 1976, Merck & Co., Inc., Rahway, NJ, monograph 8225, p, 1098.
Kovács et al. *Thrombosis and Haemostasis* (Stuttgart) 1979. 42(4), 1187–92.
McGuire et al. *Biochemistry* Feb. 1964, 3(2), 247–251.
Kimura et al. *Fukushima Journal of Medical Science* 1968, 15(1–2), 55–60.
XP–002102509 Polemical Review, Schirrmacher et al., "Importance of Cell Surface Carbohydrates in Cancer Adhesion, Invasion and Metastasis, vol. 2, No. 6, 1982, pp. 313–360.
XP–002102510 Abstract; Derwent AN 94–321291; 9–6–94.

*Primary Examiner*—Kathleen K. Fonda
*Attorney, Agent, or Firm*—Parkhurst & Wendell, L.L.P.

[57] ABSTRACT

The present invention is aimed at providing an anticancer agent which can inhibit the metastasis of cancer cells when used alone. In addition, the present invention is also aimed at providing an anticancer agent which can inhibit the metastasis of cancer cells while causing a small side effect and very small toxicity even for an extended time of administration. The cancer metastasis-inhibiting anticancer agent according to the present invention is characterized by containing sialic acid, its salt, a polymer of sialic acid or a salt of the polymer as an effective ingredient.

1 Claim, 2 Drawing Sheets

Adhesion-inhibiting effect of sialic acid

Adhesion-inhibiting effect of sialic acid

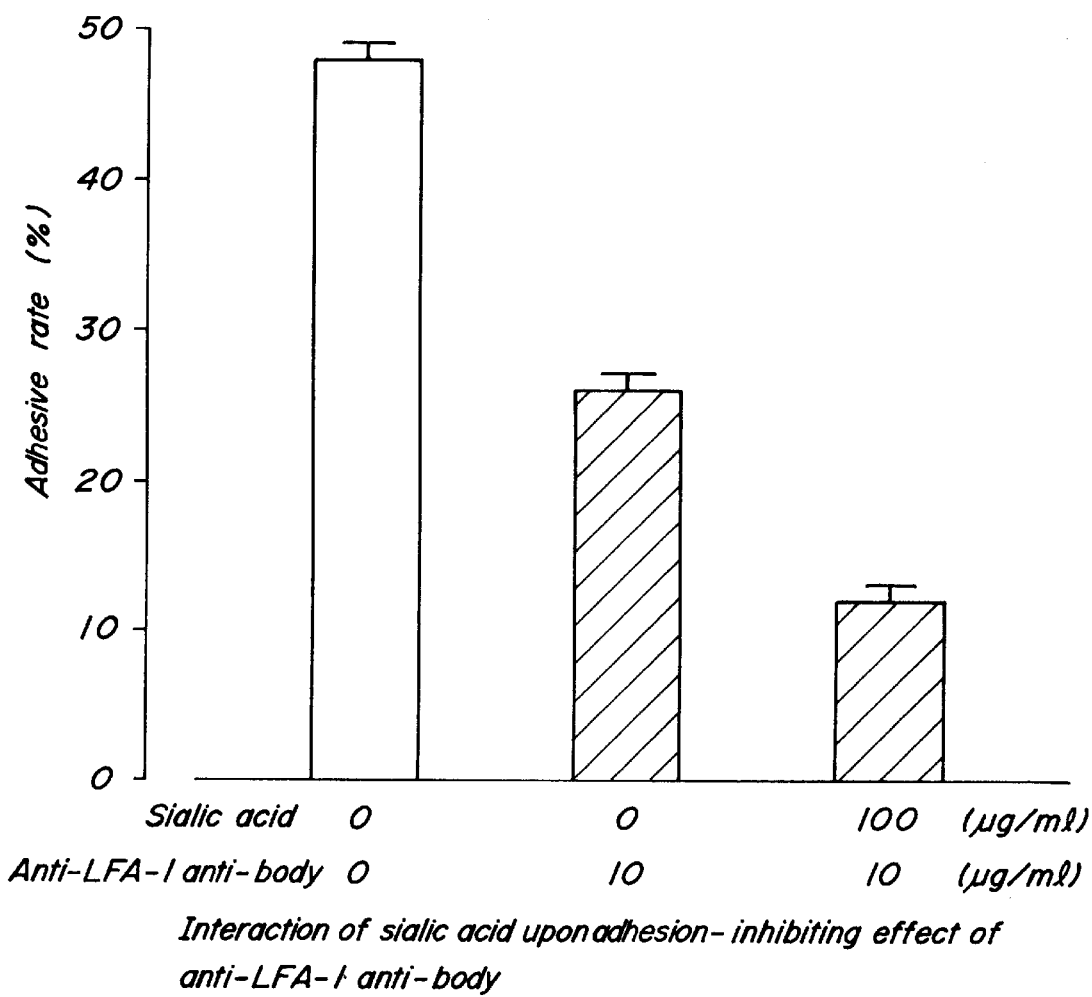
FIG_2
Interaction of sialic acid upon adhesion-inhibiting effect of anti-LFA-1 anti-body

METHOD OF INHIBITING CANCER METASTASIS this application is the U.S. national stage entry under 35 USC 371 of PCT/JP96/00268 filed Feb. 8, 1996.

FIELD OF THE INVENTION

The present invention relates to an anticancer agent for remarkably inhibiting the metastasis of cancer cells, and is aimed at providing a medicine which can completely cure a cancer by inhibiting the metastasis of the cancer cells.

BACKGROUND TECHNIQUE

In order to treat cancers, there have been recently adopted chemical therapy using various anticancer agents, immunotherapy for promoting the production of antibodies against cancer cells, surgical therapy for extracting cancer cells, radiotherapy for killing cancer cells by irradiation, etc. However, as these therapies have been developed, the surgical operations or radiotherapy technically suffer their limits, and cannot effectively inhibit the metastasis of the cancers. On the other hand, although the chemical therapy directly acts upon the cancer cells with use of the anticancer agents, many of the anticancer agents then cause harmful side effects even upon normal cells of a host. Therefore, the chemical therapy is not necessarily effective for the metastasis of the cancer. Further, no excellent effects against the metastasis of the cancers have not been seen in the case of the immunotherapy which is to treat the cancer. Although the therapeutic effects against original cancers have been largely enhanced, not a few patients become dead by metastasized cancers provoked by the metastasis of cancer cells, even if the original cancers are completely cured. In order to inhibit the metastasis of the cancers, there has strongly demanded development of medicines for inhibiting the metastasis of cancer cells. It is considered that the cancer cells metastasize over a wide area through being adhered to cell membranes of tissues such as mesenteries.

Although it is recognized that a medicine for inhibiting the metastasis of cancer cells has an effect to inhibit the metastasis of the cancer cells when sizofiran is used in combination with a chemotherapy agent, a medicine has not been commercially available to inhibit the metastasis of cancer cells when used alone. Further, although JP-A 60-190,791, JP-A 61-83,125 and JP-A 62-223,124 disclose cancer metastasis-inhibiting actions with sialic acid derivatives, they fail to describe sialic acid or its derivative used as an effective ingredient in the present invention or the cancer metastasis-inhibiting action thereof.

PROBLEMS TO BE SOLVED

In view of the above problems, the present invention is aimed at providing an anticancer agent which can inhibit the metastasis of cancer cells when used alone. In addition, the present invention is also aimed at providing an anticancer agent which can inhibit the metastasis of cancer cells while causing a small side effect and very small toxicity even for an extended time of administration.

Measure to Solve the Problems

The present invention has been accomplished through screening medicines capable of inhibiting the metastasis of cancer cells from the natural sphere, and relates to an anticancer agent having sialic acid and/or its salt as an effective ingredient and exhibiting a cancer metastasis-inhibiting action.

The present invention also relates to an anticancer agent having a polymer of sialic acid and/or a salt of the polymer as an effective ingredient and exhibiting a cancer metastasis-inhibiting action.

It is preferable that the polymer of sialic acid is a polymer composed of two to thirteen moles of sialic acid. The reason why the upper limit is set upon a thirteen molecule polymer is that it is possible to effectively fraction and separate up to the thirteen molecule polymers. It is expected that the sialic acid polymers composed of two to thirteen molecules of sialic acid and the salts thereof have pharmacological effects similar to those of sialic acid and its salt. As the salts of sialic acid and its polymers, various pharmaceutically allowable salts may be used. As the salts of a monomer of sialic acid, a sodium salt, a potassium salt, a calcium salt, and a magnesium salt may be used. As the salts of the polymers of sialic acid, sodium salts may be used. "Sialic acid" referred to in the present specification and claims means "N-acetylneuraminic acid".

As pharmaceutical preparations of the present invention, oral administration preparations such as tablets, capsules, powders, etc., percutaneous absorption preparations such as suppository, vaginal suppository, etc, and injection preparations for subcutaneous injections, intraperitoneal injections, intraveneous injections, etc. may be recited. The oral administration preparations are most preferable for the purpose of preventing diseases, whereas the injection preparations are most preferable for the purpose of emergency.

The oral administration preparations, percutaneous absorption preparations and injection preparations may be formulated according to ordinary medicine-formulating processes. Formulating examples of an oral administration preparation and an injection preparation may be recited as follows.

1) A Formulating Example of the Injection Preparation

After 50 g of sialic acid or its polymer was dissolved into 1000 ml of distilled water (free from pyrogen), a pH value of the solution was adjusted to 7.0 by using a solution of caustic soda. The resultant was filtered and sterilized according to ordinary methods. The sterilized filtrate was sealingly and aseptically charged into a 20 ml ampule, thereby obtaining an injection preparation.

2) A Formulating Example of the Oral Administration Preparation

A capsulated preparation was produced by charging 280 mg of sialic acid or its polymer having passed a 60-mesh sieve into a No. 3 gelatin capsule.

The dosage varies depending upon the age, the sex, the degree of a disease, etc. of a patient, and cannot be generally specified. With respect to sialic acid or a sodium salt of its polymer contained in an injection preparation, it may be administered at a dosage of 1–2000 mg/kg, preferably 10–500 mg/kg per day for an adult, and the number of times of administrations is one to six per day. Administration through intravenous drip infusion is also an effective measure.

Since sialic acid is a substance which is much contained in terminals of saccharides present in surface layers of cells constituting the human body and in terminals of saccharides of glycoproteins present in the blood and the body fluid, it is a medicine which causes an extremely small adverse effects against the human body.

Sialic acid and its polymers used in the present invention may be any of chemically synthesized products, enzymatically catalyzed synthesized products obtained by using sialic acid aldolase or cytosine monophosphate-N-acetylneuraminic acid (CMP-NANA) synthesis enzyme or CMP-NANA transferase, and hydrolyzed products of colominic acid obtained by decomposing colominic acid with an acid. However, sialic acid and its polymers are not limited to them.

BRIEF DESCRIPTION OF THE FIGURES

FIG. 2 shows an interaction of sialic acid upon the adhesion-inhibiting effect on the rat M-cells of the cancer cells of a LFA-1 antibody.

BEST MODE FOR CARRYING OUT THE INVENTION

Figure 1:
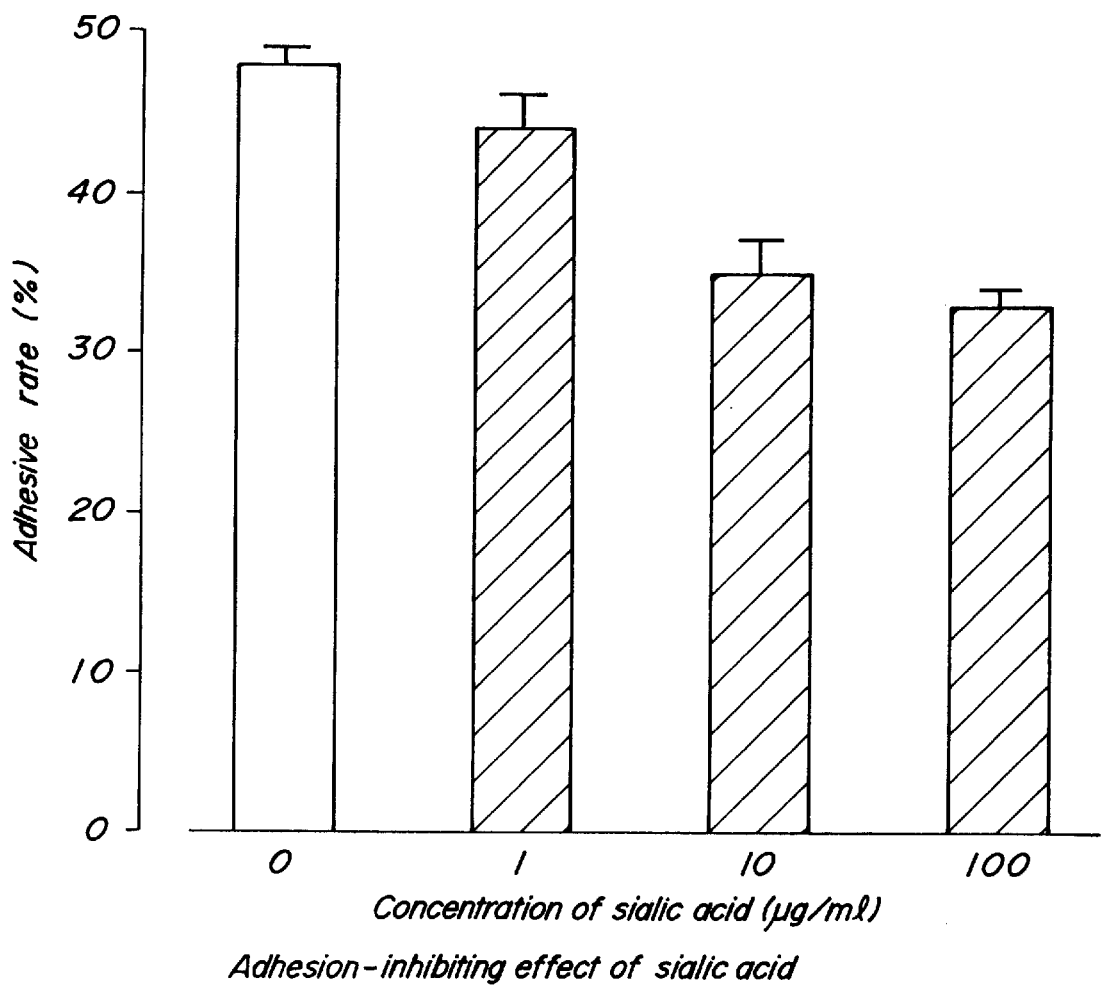
FIG. 1 shows an adhesion-inhibiting effect of sialic acid upon rat M-cells of cancer cells.

According to the present invention, sialic acid, a salt of sialic acid, a polymer of sialic acid and/or a salt of the sialic acid polymer contained as an effective ingredient in the anticancer agent inhibits the cancer cells from being adhered to the cell membranes such as mesenteries, thereby inhibiting the metastasis of the cancer cells. Sialic acid, the salt of sialic acid, the polymer of sialic acid and the salt of the sialic acid polymer may be added singly as an effective ingredient or two or more kinds of them may be used in combination.

EXAMPLES

The present inventors employed, as a model system for the measurement of the metastasis-inhibiting action upon the cancer cells, a system in which rat ascites hepatoma as extremely malignant cancer cells were adhered to mesenteries of a rat. They also employed a cell system as a simpler technique. As the former cancer cells, AH66F-cells were used, whereas M-cells were used as the latter mesentery cells.

The present inventors screened various substances present in the natural sphere by using the above-mentioned measuring system. As a consequence, they recognized that sialic acid and its polymers exhibit activity to inhibit the cancer cells from being adhered to ascites hepatoma and that conspicuous life-prolonging effect was observed in animal experiments using rats suffering AH66F ascites hepatoma. In the following, the present invention will be exemplified in more detail with reference to examples.

Example 1

Mesentery cells (M-cells) originating from a rat was cultivated inside a cell-cultivating well plate with a Dulbecco's Modification of Eagle's Medium (DMEM) containing 5% fetal calf serum (FCS). When the cells spread over the entire face of the well, the cells were washed with DMEM containing no FC3. Further, the cells were cultivated with DMEM containing 10 μg/ml or 100 μg/ml of sialic acid at 37° C. After 45 minutes passed, the well was washed with DMEM, and rat AH66F cells (4×10 cells/well) and sialic acid at a concentration shown in FIG. 1 were added together with DMEM. The mixture was cultivated at 37° C. for one hour. After the cultivation, the mixture was stirred for 30 second, and a cultivation supernatant liquid was taken into a sample tube. Into each well was added 200 μl of fresh DMEM, and washing was similarly carried out under stirring for 15 seconds. This washing operation was carried out further twice, and the used wash liquid was combined with the cultivation supernatant liquid. The resultant was subjected to centrifugal separation at 12,000 rpm for 5 minutes. After a supernatant liquid was removed, 100 μl of fresh DMEM was added to suspend the cells. Then, the number of the cells was measured by a haemacytometer under a microscope (the number of non-adhered cells).

As a control, only cancer cells were cultivated, the same operations as mentioned above were effected, and the number of the cells were measured (the number of cells in control).

The adhesive rate (%) of the cancer cells was calculated according to the following calculating formula. Results are shown in FIG. 1 in which the average adhesive rates at concentrations of sialic acid, etc. over four wells are given.

Adhesive rate=[1−(number of non-adhered cells)/(number of cells in control)]×100

As shown in Example 1, 10 μg/ml and 100 μg/ml concentrations of sialic acid inhibited the cancer cells from being adhered to mesentery cells by 27% and 31%, respectively.

Example 2

Effect of Inhibiting the Adhesion of Cancer Cells With Sialic Acid, etc. Under Coexistence of Anti-LFA-1 antibody Example 2 was examined in exactly the same manner as in Example 1 except that sialic acid at a concentration of 0 or 100 μg/ml coexisted with 10 μg/ml of anti-LFA-1 antibody in the cultivation to contact the M-cells with the AH66F cells..

Results are shown in FIG. 2.

Under coexistence of rat anti-LFA-1 antibody (antibody to β-chains of leukocyte function-associated antigen) well known as inhibiting the adhesive activity of the cancer cells, addition of no sialic acid exhibited 40% inhibition, whereas addition of 100 μg/ml exhibited 7% adhesion inhibition. This shows that the adhesion-inhibiting mechanism of sialic acid upon the cancer cells differs from that of sialic the anti-LFA-1 antibody and that a synergistic effect is attained by both the substances.

Example 3

In the model tests, it was revealed that sialic acid has the effect of inhibiting the adhesion of the cancer cells. Accordingly, effects of sialic acid and its polymer upon rats suffering metastasized cancer (AH66F) were examined.

Life-Prolonging Effect of Sialic Acid, etc. Upon the Cancer-Suffering Rats

AH66F cancer cells (1×10$^6$ cells) were each peritoneally administered to Donryu male rats (six week age, 100–120 g, each group—6 rats). Immediately thereafter, a solution of sialic acid (dosage: 10 mg/kg and 100 mg/kg) or physiological saline solution was peritoneally administered in a dosage of 0.5 ml (control group). Then, after sialic acid or physiological saline solution was peritoneally administered over 2 days, survival dates of the rats were observed.

The life-prolonging percentage was calculated according to the following formula. Results are shown in Table 1.

Life-prolonging percentage=[(survival dates of treated group)−(survival dates of control group)/(survival dates of control group]×100

TABLE 1

| Treated group | Life-prolonging effect of sialic acid upon rats with AH66F cancer cells | | |
|---|---|---|---|
| | | Survival dates | Life-prolonging percentage |
| Control | | 7.3 ± 0.3 | — |
| Sialic acid | 10 mg/Kg × 3 days | 11.5 ± 0.4 | 58% |
| | 100 mg/Kg × 3 days | 13.4 ± 0.4 | 84% |

As a result, it was confirmed that the control group administered with no sialic acid, etc. exhibited the survival dates of 7.3 ±0.3, the group administered with 10 mg/Kg of sialic acid exhibited the life-prolonging effect by 1.6 times as much as that of the former, and the group administered with 100 mg/Kg of sialic acid exhibited the life-prolonging effect by 1.8 times.

Acute Toxicity Test

LD50 in the case of the intraveneous administration to a Wister-strain rats (male) was determined, according to which the sodium salts of sialic acid and its trimer (pH 7.0) both revealed not less than 2,000 mg/Kg.

What is claimed is:

1. A method of inhibiting a cancer metastasis comprising administering to a patient in need thereof a cancer metastasis-inhibiting effective amount of a polymer composed of 2 to 13 molecules of N-acetylneuraminic acid.

* * * * *